United States Patent [19]

Casellas et al.

[11] Patent Number: 4,643,895
[45] Date of Patent: Feb. 17, 1987

[54] ANTI-CANCER DRUGS FOR THE TREATMENT OF LEUKAEMIAS I, CONSTITUTED BY THE CHAIN A OF RICIN AND A SPECIFIC MONOCLANAL ANTIBODY

[75] Inventors: Pierre Casellas; Pierre Gros, both of Montpellier; Franz Jansen, St. Mathieu de Treviers, all of France

[73] Assignee: Sanofi, Paris, France

[21] Appl. No.: 438,037

[22] Filed: Nov. 1, 1982

[30] Foreign Application Priority Data

Nov. 20, 1981 [FR] France ................................ 81 21836

[51] Int. Cl.⁴ ...................... A61K 39/00; A61K 35/78
[52] U.S. Cl. .......................................... 424/85; 424/88
[58] Field of Search ............................ 424/85, 86, 89; 435/172, 240, 241, 948

[56] References Cited

PUBLICATIONS

Royston et al., J. of Immunology, 125 (2), 725–731 (1980).

Blythman et al., Nature, vol. 290, pp. 145–146, Mar. 12, 1981.

Primary Examiner—Shep K. Rose
Attorney, Agent, or Firm—Walter H. Schneider

[57] ABSTRACT

The present invention relates to an anti-cancer drug, characterized in that it contains at least one product constituted by the chain A of recin conjugated by means of a disulfide bridge with at least one fraction of a monoclonal antibody of leukaemic anti-cell specificity, and to the processes for preparing the active ingredient of said drug.

3 Claims, No Drawings

ANTI-CANCER DRUGS FOR THE TREATMENT OF LEUKAEMIAS I, CONSTITUTED BY THE CHAIN A OF RICIN AND A SPECIFIC MONOCLANAL ANTIBODY

The present invention relates to novel anti-cancer drugs for the treatment of leukaemias T, constituted by the chain A of ricin and by a specific monoclonal antibody.

The preparation of so-called conjugate anti-cancer products obtained by coupling, by means of a covalent bond the chain A of ricin with a protein structure such as an antibody, e.g., an immunoglobulin or a fragment of immunoglobulin, capable of selectively recognizing a given antigen on the surface of the carrier cells which it is desired to reach such as the cancerous cells. The main property of these conjugates is that they are cytotoxic agents specific of the target cells aimed at.

The use of antibodies directed against the antigens for differentiation of the cancerous cells had already made it possible to obtain conjugates presenting a considerable specificity with respect to the target cells.

The present invention relates to so-called conjugate products obtained from the chain A of ricin and a human anti-cell T monoclonal antibody.

Conjugates are understood to mean artificial mixed molecules in which the chain A of ricin is associated by a covalent bond of disulfide type with a human anti-cell T antibody capable of selectively recognizing an antigen associated with cancerous cells.

The manner in which the chain A of pure ricin is obtained has been described in U.S. Pat. No. 4,340,535. The preparation of monoclonal antibodies directed against human leukaemic T cells has been mentioned in scientific literature. (Particular reference may be made to the Journal of Immunology 125) (2), 725-731 (1980).

To make the conjugates, the proteins to be coupled must each carry at least one atom of sulfur naturally capable or artificially rendered capable of creating the desired disulfide bond.

The chain A of ricin naturally presents one single atom of sulfur allowing the desired coupling. It is that of the thiol function of the cysteine residue included in the chain A and which ensured the bond of this chain A to the chain B in the complete toxin.

The whole antibody of human anti-cell T specificity comprises neither free thiol function nor other atoms of sulfur capable of being used for coupling. If this whole antibody is used, it will therefore be expedient artificially to introduce on the molecule of immunoglobulin one or more atoms of sulfur capable of subsequently being engaged in the disulfide bond to be established with one or more molecules of chain A of ricin.

If, on the other hand, the fragment Fab' of this antibody is used as is conventionally obtained by limited proteolysis in the presence of pepsin followed by a reduction of the (or each) disulfide bridge between heavy chains, this fragment then presents at least one available thiol group for creating the disulfide bridge with the chain A of ricin. In this latter case, according to the invention, the thiol group available on the fragment of antibody will generally be converted by known methods into activated mixed disulfide, before being reacted with the thiol of the chain A to create the desired disulfide group.

If the whole antibody is used, according to the invention, the preparation of the conjugate is effected by bringing together the chain A of ricin carrying its free SH group and the antibody in which the SH group has been artificially introduced in activated form and particularly in the form of a mixed disulfide with a suitable sulfured organic radical.

The preparation of the conjugate may then be represented by the scheme:

$$RA-SH + AC-R-S-S-X \rightarrow$$
$$RA-S-S-R-AC + XSH$$

in which:

RA designates the chain A of ricin

AC designates the antibody

X designates the activator radical.

The antibody substituted by an activated sulfur atom is obtained from the antibody itself, by substitution with the aid of a reagent (itself carrier of an activated sulfur atom) according to the scheme:

$$AC + Y-R-S-S-X \rightarrow AC-R-S-S-X$$

in which:

AC designates the antibody

Y represents a function allowing covalent fixation of the reagent on the protein R designates a group which may simultaneously carry the substituents Y and —S—S—X X designates the activator radical.

The functional group Y is a function capable of bonding covalently with any one of the functions carried by the side chains of the amino-acids constituting the protein to be substituted. From among these, the terminal amino functions of the lysyl radicals contained in the protein are particularly indicated. In this case, Y may represent, in particular:

a carboxylic group which may bond with the amino functions of the protein in the presence of a coupling agent such as a carbodiimide and in particular a water-soluble derivative such as 1-ethyl-3(3-diethyl-amino propyl)carbodiimide, a chloride of carboxylic acid which is capable of reacting directly with the amino functions to acylate them, a so-called "activated" ester such as an ester of ortho- or para-, nitro- or dinitro-phenyl or an ester of N-hydroxy succinimide which reacts directly with the amino functions to acylate them, an internal anhydride of a carboxylic diacid such as for example succinic anhydride which reacts spontaneously with the amine functions to create amide bonds, an imidoester group

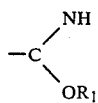

where $R_1$ is an alkyl group reacting with the amino groups of the protein according to the reaction

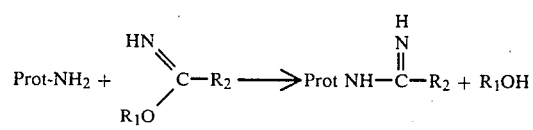

The radical —S—S—X designates an activated mixed disulfide capable of reacting with a free thiol radical. In particular in this mixed disulfide, X may designate a 2-pyridyl or 4-pyridyl group possibly substituted by one or more alkyl, halogen, carboxylic radicals. X may also designate a phenyl group preferably substituted by one or more nitro- or carboxylic groups. X may further represent an alkoxycarbonyl group such as the methoxycarbonyl group.

The radical R designates any radical capable of simultaneously carrying the substituents Y and S—S—X. It must be selected so as not to comprise any functions capable of interfering in the course of the subsequent reactions with the reagents used and the synthesized products. In particular, the group R may be a group —$(CH_2)_n$ with n included between 1 and 10, or a group:

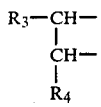

in which $R_4$ designates hydrogen or an alkyl group having from 1 to 8 atoms of carbon and $R_3$ designates a substituent which is inert with respect to the reagents used subsequently such as a carbamate group

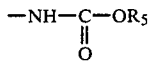

where $R_5$ designates a straight or branched alkyl group having from 1 to 5 atoms of carbon and particularly the tertiobutyl group.

The reaction of the compound Y—R—S—S—X with the immunoglobulin is carried out in homogeneous liquid phase, most often in water or a buffer solution. When the solubility of the reagents requires this, it is possible to add to the reaction medium up to 20% by volume of a water-miscible organic solvent such as an alcohol and particularly tertiary butanol.

The reaction is carried out at ambient temperature for a period of time varying from a few hours to 24 hours. After which a dialysis makes it possible to eliminate the products of low molecular mass and, in particular, the excesses of reagents. This process makes it possible to introduce a number of substituent groups per mole of protein of between 1 and 5 if the protein is an immunoglobulin of class G, and of between 1 and 15 if the protein is an immunoglobulin of class M.

By using such compounds, the coupling with the chain A of ricin is effected by bringing together in aqueous solution the two proteins at a temperature not exceeding 30° C. for a period of time varying from a few hours to a day. The solution obtained is dialysed to eliminate the products of low molecular mass, then the conjugate may be purified by various known methods.

The following example will enable the invention to be more readily understood without limiting the scope thereof.

EXAMPLE 1

Conjugate obtained by reaction between a human anti-cell T antibody (antibody directed against the antigen T65) substituted by an activated disulfide group and the chain A of ricin.

(a) Human anti-cell T antibody (or antibody T101)

This antibody was obtained according to the method described in the Journal of Immunology 125 (2), 725–731 (1980).

It undergoes ultimate purification by dialysis against a PBS buffer (10 mM of phosphate, 140 mM of sodium chloride, pH 7.4).

(b) Chain A of ricin:

The chain A of ricin was prepared and purified as indicated.

(c) Activated human anti-cell T antibody:

To 0.5 ml of a solution of 14.2 mg/ml of 3-(2-pyridyl disulfanyl)propionic acid in tertiobutanol is added 0.1 ml of a solution of 42.7 mg/ml of 1-ethyl 3(3-dimethylamino propyl)carbodiimide and the solution is left for 3 minutes at ambient temperature.

180 μl of the solution thus obtained are added to 5.6 ml of a solution of antibody at 3.6 mg/ml in the PBS buffer. Incubation is allowed to continue for 20 hours at 30° C.

The solution is then continuously dialysed for 3 days against 21 liters of PBS buffer at 4° C. 16 mg of activated antibody are thus obtained at a concentration of 2.6 mg/ml.

By spectrophotometric assay at 343 nm of the pyridine 2-thione released by exchange with the reduced glutathion, it is observed that an antibody carrying 3.1 activator groups per mole of antibody is obtained.

(d) Conjugate:

To 4.6 ml of a solution of activated antibody in the PBS buffer (concentration 2.6 mg/ml, or 12 mg of activated antibody) is added 0.87 ml of a solution of chain A of ricin in the same buffer (concentration 6.6 mg/ml) and incubation is carried out at 25° C. for 20 hours.

The reaction mixture is chromatographed over a Sephadex G100 gel column. In each fraction, the concentration in antibody is determined by spectrophotometry at 280 mm and that of the chain A is determined by its power of inhibition of the proteosynthesis measured on an acellular system. The identical fractions containing the conjugate are brought together and about 11 mg of the conjugate at the concentration of 0.8 mg/ml are obtained.

The analytic determinations made show that the solution contains 140 μg/ml of biologically active chain A, or about 1.1 mole of chain A per mole of antibody.

A study made by cytofluorometry further showed that the human anti-cell T antibody used, the corresponding activated antibody and the conjugate of this antibody with the chain A of ricin present superposable histograms of fluorescence which affirm that the antibody has not undergone any considerable alteration in the course of the reactions of activation and of coupling to which it was subjected and in particular that it remains capable, within the conjugate itself, of recognizing the human antigen T against which it is directed.

The conjugate according to the invention, obtained previously, was studied for its biological properties and more especially for its anti-cancer action.

(1) INHIBITION OF PROTEOSYNTHESIS

The fundamental biological property of the chain A of ricin is that it inhibits the cellular proteosynthesis by alteration of the ribosomal sub-unit 60 S.

A cellular model was used here. This test measures the effect of the substances studied on the incorporation of $^{14}C$-leucine in the cancerous cells in culture.

The cells used belong to the cellular stock CEM issuing from a human leukaemia T which carries the antigen T65. The cells are incubated in the presence of the substance to be studied then, at the end of incubation, the rate of incorporation of $^{14}$C-leucine by the cells thus treated is measured.

This measurement is effected according to a technique adapted from the technique described in the Journal of Biological Chemistry 1974, 249 (11), 3557-62 using the $^{14}$C-leucine tracer for determining the rate of proteosynthesis. The determination of the incorporated radioactivity is here effected on the whole cells isolated by filtration.

From these determinations, the dose/effect curves can be plotted, the x-axis showing the molar concentration of chain A of the substances studied and the y-axis the incorporation of $^{14}$C-leucine expressed as percentage of the incorporation of the control cells in the absence of any substance affecting the protein synthesis.

For each substance studied, the concentration which inhibits 50% of the incorporation of $^{14}$C-leucine or "inhibitory concentration 50" (IC 50) may thus be determined.

The FIGURE shows the curves obtained in the same experiment with ricin, with its free chain A and with the conjugate RT2 (compound prepared according to Example 1), in the presence and in the absence of 10 mM ammonium chloride in the incubation medium. Even in the absence of ammonium chloride and after incubation of 48 hours, it may be observed from this Figure that the conjugate RT2 studied has a considerable cytotoxic activity (IC 50 = $7 \times 10^{-12}$M), about 7000 times greater than that of the chain A of ricin.

(2) POTENTIALIZATION OF THE ACTIVITY OF THE CONJUGATE RT2 BY AMMONIUM CHLORIDE

As is also shown in the FIGURE, the presence of 10 mM ammonium chloride in the incubation medium of the cells with the conjugate RT2, increases the cytotoxic activity of the conjugate on the target cells considerably—about 80 times. This potentializer effect is not obtained either with the ricin, or with the chain A, or with a non-specific conjugate of the cells studied. In this way, in the presence of ammonium chloride as potentializer agent, the cytotoxic activity of the conjugate (IC 50 = $8.5 \cdot 10^{-14}$M) becomes about 600,000 times greater than that of the chain A alone and even exceeds in power the activity of the ricin, which has never been described for any conjugate between the chain A of ricin and any antibody.

The conjugates prepared according to the invention show, per se, a considerable cytotoxic activity specific with respect to the cellular stocks of human leukaemias T. They may therefore be used in human therapeutics in the treatment of leukaemias T or any other disorder, cancerous or not, in which cells which are sensitive to the conjugate prepared according to the invention are to be selectively destroyed. This can be envisaged in transplants or certain auto-immune diseases to reduce the activity of the lymphocytes T or such sub-population of lymphocytes T.

If account is further taken of the very considerable potentializer effect of the ammonium chloride on the activity of these conjugates with respect to the corresponding target cells, it is possible to take advantage of this novel property with a view to increasing the therapeutic efficacy of the conjugate in the treatment of diseases to which it is applied. This improvement may be exploited according to two different therapeutic schemes:

(a) Samples of human bone marrow coming from leukaemia sufferers may be treated in vitro by the conjugate RT2 in the presence of ammonium chloride. As this association presents a very considerable and very specific cytotoxic efficacy, it is possible to eliminate from the marrow thus treated any cell carrying the antigen recognized by the conjugate and in particular any tumoral cell.

Furthermore, the patient may be treated by any appropriate therapy such as radiotherapy and/or chemotherapy at above-lethal dose so as to eliminate the tumoral cells from his organism. Finally, the marrow, purified as indicated, is again transplanted in the patient's organism in the form of autologous graft to allow reconstitution of the populations of blood cells destroyed by the above-lethal treatment.

(b) The application of the potentializing property of the ammonium chloride in the patient in vivo may also be exploited to obtain the maximum efficacy of the conjugate. In fact, it has been shown that mice in which tumoral cells were previously transplanted and to which the conjugate is administered at the same time as 3 injections of 7 mg of ammonium chloride at intervals of 15 minutes, show a better percentage of survival and a better tumour growth inhibition than the control mice having received the conjugate alone.

These conjugates are prepared for administration by the injectable route. They may be used either alone, associated with the ammonium chloride or associated with another treatment for the cancerous disorder in question and, in particular, associated with other immunosuppressive drugs in order to delay and weaken the natural immunitary reaction of the patient to the protein, represented by the conjugate, foreign to his organism.

It purpose being to eliminate all the cancerous cells, the treatment must be effected with a sufficient dose of conjugate and the duration of the treatment must be determined in each case as a function of the subject and the nature of the disorder to be treated.

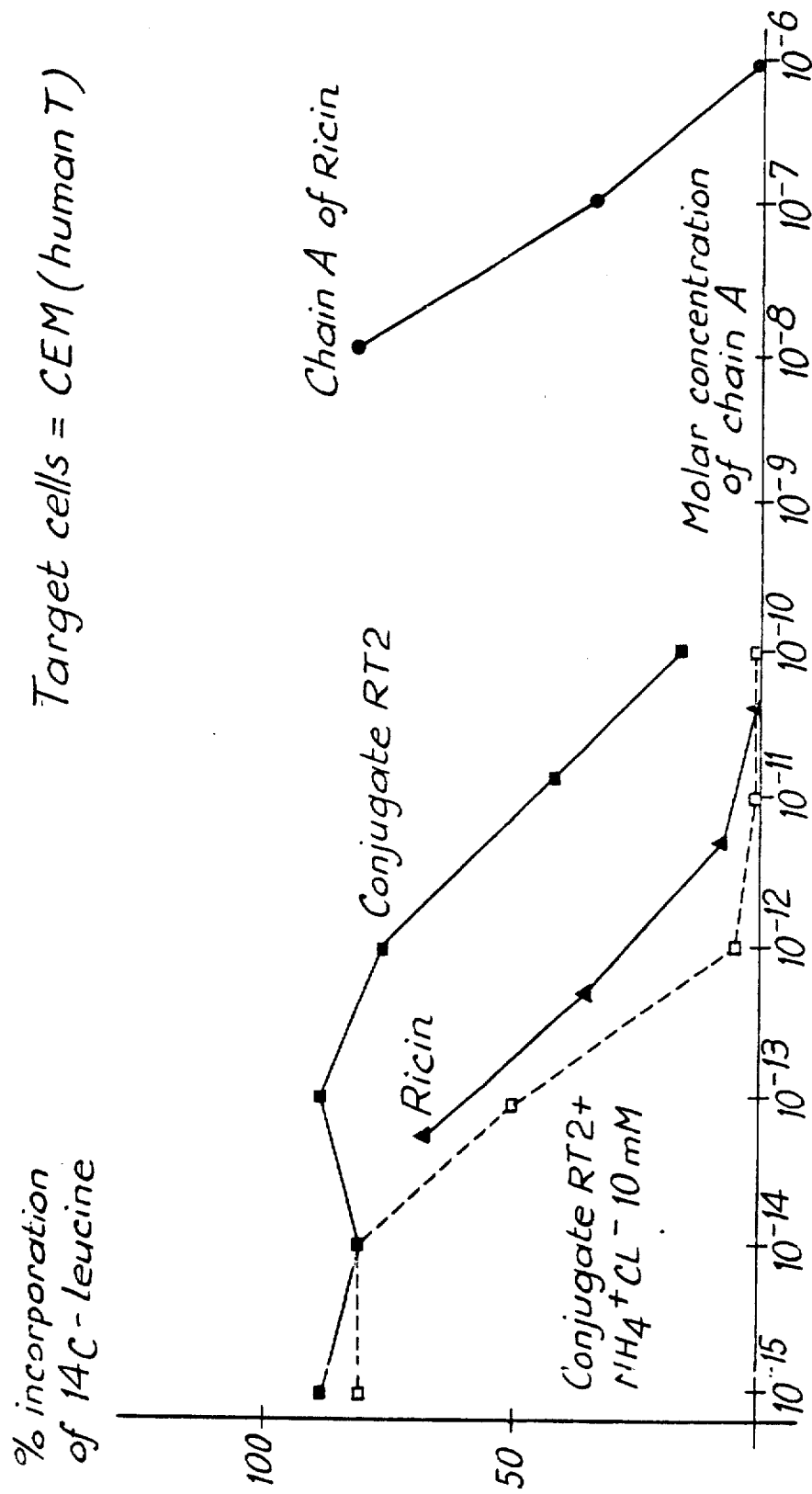

What is claimed is:

1. An anti-cancer composition comprising a conjugate of the chain A of ricin coupled by means of a disulfide bridge with at least one fraction of a monclonal antibody T101 of human leukaemic anti-cell specificity.

2. A composition according to claim 1 which includes an amount of ammonium chloride to effectively increase the therapeutic activity of said conjugate.

3. A composition according to claim 2 in which the monoclonal antibody is the fragment Fab' of the antibody.

* * * * *

UNITED STATES PATENT AND TRADEMARK OFFICE
CERTIFICATE OF CORRECTION

PATENT NO.   :   4,643,895

DATED        :   February 17, 1987

INVENTOR(S)  :   Pierre Casellas et al.

It is certified that error appears in the above-identified patent and that said Letters Patent is hereby corrected as shown below:

The title of invention should read -- ANTI-CANCER DRUGS FOR THE TREATMENT OF LEUKAEMIAS T, CONSTITUTED BY THE CHAIN A OF RICIN AND A SPECIFIC MONOCLONAL ANTIBODY --.

The single sheet of drawing should appear as shown on the attached sheet.

On the title page, "3 Claims, No Drawings" should read -- 5 Claims, 1 Drawing Figure --.

Claim 1, line 4, cancel "T101".

Add Claims 4 and 5:

-- 4. A composition according to claim 2 in which the monoclonal antibody is the T101 antibody.

5. The process for preparing the conjugate of the composition of claim 3 in which the fragment Fab' of the antibody is converted into an activated mixed disulfide which is then reacted with the thiol of the chain A of ricin. --.

Signed and Sealed this

Twenty-second Day of December, 1987

Attest:

DONALD J. QUIGG

Attesting Officer            Commissioner of Patents and Trademarks